United States Patent [19]

Fuchs

[11] Patent Number: 4,610,966

[45] Date of Patent: Sep. 9, 1986

[54] DANSYL CHLORIDE TESTING METHOD

[75] Inventor: Alfred E. Fuchs, Denville, N.J.

[73] Assignee: Potters Industries, Inc., Hasbrouck Heights, N.J.

[21] Appl. No.: 613,593

[22] Filed: May 23, 1984

[51] Int. Cl.$^4$ ............................................. G01N 21/78
[52] U.S. Cl. ........................................... 436/2; 436/5; 436/89; 436/111; 436/172
[58] Field of Search ................... 436/2, 5, 89, 90, 172, 436/164, 111; 73/104, 105

[56] References Cited

U.S. PATENT DOCUMENTS 3,837,806 9/1984 Ritter et al. ............................. 436/2

FOREIGN PATENT DOCUMENTS 0110956 8/1980 Japan ..................................... 436/89
0110955 8/1980 Japan ..................................... 436/172

OTHER PUBLICATIONS

The Merck Index, Tenth Edition, Merck & Co., 1983, p. 406.
Bradley et al., Analytical Chemistry, vol. 31, No. 11, Nov. 1959, pp. 1925-1926.
Lehninger, A. L. Biochemistry, (Worth Publishers, 1970) p. 80.

Primary Examiner—Arnold Turk
Attorney, Agent, or Firm—Lee C. Robinson, Jr.

[57] ABSTRACT

A method of analyzing molecular layers of amino-functional group coupling agents on inorganic substrates is disclosed. A saturated solution of 1-dimethylaminonaphthalene-5-sulfonyl chloride is added to a sample to be tested, and sufficient time is allowed, with or without heating, for the reaction of the 1-dimethylaminonaphthalene-5-sulfonyl chloride with any amino functional group coupling agent which might be present. The color intensity of the reaction product is compared under ultraviolet light in an otherwise substantially dark room with the color intensity of standards representative of known thicknesses of coupling agent to determine the existence and thickness of the coupling agent on the particles being analyzed. If the reaction is allowed to progress without heating, rinsing will wash away some of the coating that is not sufficiently chemically bound to the substrate, and thus will decrease the amount of reaction product - of which the coating is a substituent - that can be observed on the substrate. The reduced reaction product is manifested by a reduced color intensity of the sample when viewed under ultraviolet light in a dark room. The occurrence of this reduced color intensity, relative to a part of the same sample reacted with heating, indicates insufficient chemical bonding of the coating to the substrate.

7 Claims, No Drawings

DANSYL CHLORIDE TESTING METHOD

BACKGROUND OF THE INVENTION

This invention relates to the analysis of organic coating materials on inorganic substrates, and more particularly to a method of analyzing molecular layers of amine-type coupling agents on glass spheres and other discrete particles.

The present invention, while of general application, is particularly well-suited for use in the qualitative and quantitative analysis of amino functional group silane coatings on small glass spheres. Coatings of this type are commonly applied to the spheres to enhance the bonding of the inorganic glass substrate to resinous materials. The substrate is thus made available for a variety of uses. A typical use involves the providing of retroreflectance for highways. In cases in which the spheres are to be used as fillers in nylon, polyphenylene oxide, paints, alkyds, epoxies, chlorinated rubber, or other polymers, for example, the coating improves the dispersibility of the glass in the resin and provides positive adhesion therebetween.

The amount of coupling agent applied to the individual glass spheres must be carefully controlled. The spheres are unique because of their nonporous surface and small size, small glass spheres typically ranging between 6 and 800 microns in diameter depending on their final application. Each sphere must be completely coated with at least one molecular layer of coupling agent to provide a satisfactory bond. If the thickness of the coating exceeds about five molecular layers, however, there is too great a quantity of coupling agent to provide an effective bond, manifesting itself in less satisfactory physical properties of the end product. Additionally, the excess coupling material is wasted when more than five layers are present.

Heretofore, difficulties have been encountered in analyzing these small amounts of coupling agents on glass spheres and other nonporous inorganic substrates. Conventional analytical techniques have proved deficient particularly in the measurement of coupling agents from both the qualitative and quantitative standpoints. Also the inaccuracy, low sensitivity, and high cost of such techniques has rendered them impractical in the analysis of the coupling agents used in many present day bead coating systems. The problems encountered with the testing procedures previously employed have been of special moment in the manufacture of coated beads on an industrial mass-production basis, with the result that the end product occasionally exhibited a coating that was too thin to provide the desired coupling action or that unnecessarily large quantities of the coupling agent were consumed.

In U.S. Pat. No. 3,837,806, Ritter et al disclosed a method of analyzing molecular layers of an amino silane coupling agent on glass spheres, in which a saturated solution of 1-chloro-2,4-dinitrobenzene in methyl alcohol is added to a sample of the spheres without substantial aggitation, and the materials are then heated to a temperature sufficient to react the 1-chloro-2,4-dinitrobenzene with the coupling agent. Ritter et al then compared the yellow color of the reaction product with successive color standards representative of known thicknesses of silane layers in order to determine the thickness of the layers on the spheres being analyzed.

The method disclosed by Ritter et al., however, is not sufficiently accurate for many desired analyses, particularly the detection of relatively low concentrations of coupling agents. At low concentrations of less than one molecular layer of coupling agent, the intensity of the yellow color of the product of the reaction between the coupling agent and 1-chloro-2, 4-dinitrobenzene is too low to be observed by visual examination. Thus a qualitative analysis using the method of Ritter et al. inaccurately fails to detect the existence of coupling agents when such coupling agents are present at concentrations of less than one molecular layer. The inability of the Ritter et al. test to detect small concentrations of coupling agent leads to an increased degree of inaccuracy even in quantitative measurements since small differences in the concentration of coupling agent may have too subtle an affect upon the color of the reaction product to be readily observable.

It is accordingly an object of the present invention to provide a method of analyzing molecular layers of coupling agents on non-porous inorganic substrates with greater precision than was possible under the prior art.

It is another object of the invention to provide a method of detecting low concentrations of less than one molecular layer of coupling agent on inorganic substrates.

It is another object of the invention to provide a method for determining the presence and thickness of amino functional group silane coupling agents on glass spheres and similar discrete particles.

A further object of the invention is to provide a method for determining the strength and extent of chemical bonding between coupling agents and inorganic substrates coated therewith.

Still another object of the invention is to provide a method of evaluating amino silane coupling agents on glass spheres which method may be quickly and easily performed in a rapid and inexpensive manner.

STATEMENT OF THE INVENTION

In a typical embodiment of the invention, a test sample is formed using glass spheres coated with an amino functional group coupling agent. Other common substrates coated with agents detectable with the present invention include, without limitation, irregular glass particles, mica, alumina, and fiberglass. A saturated solution of 1-dimethylaminonaphthalene-5-sulfonyl chloride (hereinafter dansyl chloride) in acetone or other polar organic solvent is added to the sample. The solution and the sample are heated to a temperature sufficient to react the dansyl chloride with the coupling agents on the sample and produce a reaction product which exhibits a yellow-green fluorescence under ultraviolet light in an otherwise dark room. Such fluorescence indicates the presence of amine groups and thus of the amine coating. The intensity of the fluorescence is compared with successive known standards representing amine coatings of acceptable and unacceptable thicknesses.

Depending upon the number and the range of the standards used, the method of the present invention can differentiate among 0, ½, 1, 2, 5, 10, as well as numerous other numbers of, molecular layers of the coating agent on the spheres. It may be rapidly performed and is readily usable as a routine quality control procedure in the commercial manufacture of coated glass spheres and other discreet particles without the need for elaborate laboratory apparatus.

Detection of small concentrations of coupling agent and detection of small changes in concentration are made possible by the method's production of ultraviolet sensitive compounds, together with observation of those compounds under a high energy light source.

The method is such that it can be performed at elevated or ambient temperatures. This allows not only the determination of the existence of coupling agent on the surface of tested substrates, but also the determination of the firmness of the bonding between coupling agent and substrate. The invention can be used to differentiate between coating agents which are chemically bound to their substrate and those which are absorbed on the surface by secondary bonding forces only. The coupling agents are more effective when chemically bound, and chemical bonding is preferred for that reason. When the reaction of the present invention takes place with heating, preferrably for a period of approximately 15 minutes at 50° to 60° C., the dansyl chloride modified coupling agent is grafted or condensed onto the surface of the inorganic substrate. When the reaction of the present invention is allowed to proceed without heating, no such grafting or condensation occurs and the product, to the extent that it is not chemically bound to the substrate, can be rinsed off of the substrate. The determination made possible by the present invention can be achieved by dividing a sample to be tested into two parts, and carrying out the reaction of the invention at ambient temperatures as to one part and with heating as to the other part. Rinsing each part after the reaction occurs will rinse away product only from the unheated part, and only product which was formed by reaction with coating agent that was not chemically bound. The difference in the concentration of product on the two parts represents the difference between the total concentration of coupling agent and the concentration of coupling agent which is chemically bound to the substrate. This difference, if any, would be manifested by a difference in color intensity of the two samples when viewed under ultraviolet light in a substantially dark room. Any observable difference indicates the existence of coupling agent that is not chemically bound to its substrate.

The present invention as well as further objects and features thereof, will be understood more clearly and fully from the following description of certain preferred embodiments.

DESCRIPTION OF CERTAIN PREFERRED EMBODIMENTS

In a preferred embodiment of the invention, the coupling agent to be analyzed is in the form of a gamma-aminopropyltriethoxy silane coating on glass spheres. Coatings of this type exhibit particular affinity for polymeric materials with which the spheres are often used. In addition to glass spheres, the invention is also applicable to the detection and analysis of amine coupling agents on fiberglass and fillers as well as other particulate substrates. It is highly advantageous in the detection of coupling agents containing amino functional group silanes. The particular coupling agent used will depend on the purpose and properties of the material to which the substrate is to be added. Such agents and their properties are well known in the art.

The spheres to be analyzed should be of similar size distribution, particularly where the readings are to be quantitative as well as qualitative. A sample of the coated spheres is prepared by selecting the spheres in accordance with standard sampling techniques from spheres coated and processed during a production line run. The selected sample is checked for screen size and is then split to obtain a fixed fraction, illustratively 1 gram.

To form the test solution, a measured quantity of dansyl chloride is dissolved in organic solvent. Preferred solvents include reagent grade acetone, tetrahydrofuran, methanol, ethanol, propanol and isopropanol. Although the quantity of solvent used will depend on such factors as the type of solvent and the size of the selected sample, it is important in assuring high accuracy for quantitative analyses that the solution be fully saturated.

Thus prepared, the solution is added to the selected sample of glass spheres while avoiding substantial agitation. The amount by weight of solution used advantageously should be about 20% of that of the sample. Thus for a one gram sample, particularly good results are achieved by the addition of 0.2 grams of liquid.

For a quantitative or qualitative analysis of the existence of coating and of the thickness of coating, the solution and the sample can be heated in an oven, preferably for approximately 15 minutes, at a temperature of between 50° and 60° C. Excessive heating above 60° C. will result in undesirable burning that will impair the accuracy of the quantitative analysis. If it is desired to test the extent of chemical bonding between the coating and substrate, a portion of the sample will have been separated either before or after addition of dansyl chloride solution. This portion of the solution and sample is not heated, but rather is allowed to react under ambient conditions.

A typical reaction scheme undergone by the samples, with or without heating, is represented by the following general formula:

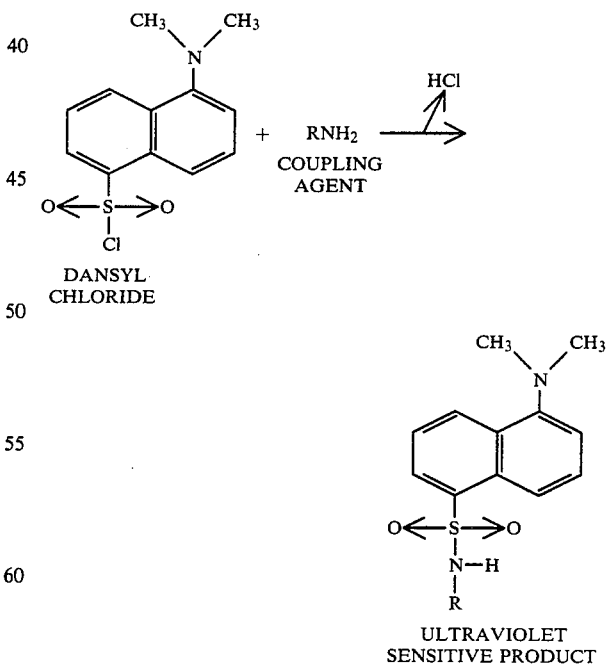

In the above formula R represents the bulk of the coupling agent to which the amine group is attached and can comprise any of a variety of known constituents. Although the formula shows only the reaction of a primary amine with the dansyl chloride, similar reactions occur with coupling agents having secondary and tertiary amine groups. As used herein and in the appended claims, the term "amino functional group" includes the group —$NH_2$ as well as mono and disubstituted amino groups such as —$NHR$ and —$NR_1R_2$, wherein $R_1$ and $R_2$ can be identical or dissimilar and wherein R, $R_1$ and $R_2$ represent any of a variety of groupings attached to the amino nitrogen in conventional coupling agents. Representative amino functional group coupling agents that may be employed include aminoalkyl trimethoxy silane, N-(beta-aminoethyl)-gamma-aminopropyl trimethoxy silane, triamino alkyl trimethoxy silane, N-bis-(beta-hydroxyethyl)-gamma-aminopropyl triethoxy silane, gamma-aminopropyl trimethoxy silane, and gamma-aminopropyl triethoxy silane. These coupling agents are illustrative of a wide variety of commercially available coupling agents with which the invention may be used.

The products of the reaction described produce a distinct yellow-green color when viewed under ultraviolet light in an otherwise dark room. The intensity of the color varies in accordance with the extent of the reaction and is an indication of the amount of amine coupling agent present in the solution. By comparing the color intensity of the reaction products with successive standards representative of known quantities of the coupling agent, the amount of coupling agent in the sample may be readily determined.

In a preferred embodiment of the invention three standards are utilized in the form of glass spheres having uniform coatings of one, two and five molecular layers of gamma-aminoproplytriethoxy silane, respectively. The quantity, size, and distribution of the spheres in each standard should be similar to the quantity, size, and distribution of the spheres being tested, and the respective thicknesses of the coatings should be accurately determined. Fresh dansyl chloride solution is added to each of the three standards in the same proportions used for the unknown sample. The standards and the sample are simultaneously heated to produce the above-described reaction, and the color intensity of the reaction product from the tested samples is successively compared under ultraviolet light with the color intensity of the standards when they are in side-by-side relationship with one another in a darkened room.

By contrasting the color intensities of the unknown sample with that of the successive standards, the presence and approximate thickness of the gamma-aminopropyltriethoxy silane on the sample may be readily ascertained. The absence in the reaction product of a yellow-green color when viewed under ultraviolet light indicates that the spheres of the sample do not have an amine type coating. If a yellow-green color is observed but its intensity is less than the one molecular layer standard, the coating on the sample is of the amine type but is less than one molecular layer in thickness. If the yellow-green intensity of the sample lies between the intensity of the one, two and five molecular layer standards, the thickness of the sample's amine coating may be bracketed accordingly, while if the observed color is a more intense yellow-green than the five molecular layer standard the coating thickness is above five molecular layers.

For most present-day applications the thickness of the amine coating on the spheres should be between one and two molecular layers and in any event less than five molecular layers. If the coating thickness is less than one molecular layer there would be an insufficient bond between the inorganic substrate and any polymer or resinous material, to which it is desired that the substrate be bound. A thickness in excess of five molecular layers similarly prevents a strong substrate-polymer bond and represents a wastage of the coating material. For best results the thickness of the coating should be maintained at about two molecular layers.

The following examples are set forth in illustration of this invention and should not be construed as limitations thereof. Unless otherwise indicated, all parts and percentages given are by weight.

EXAMPLE 1

Dansyl Chloride (0.2 grams) was added to 25 milliliters of acetone and the resulting solution was used to saturate a 10 gram sample of glass beads which were coated with an unknown amount of gamma-aminopropyltriethoxy silane coupling agent. Saturation was accomplished by adding approximately 2 milliliters of the dansyl chloride solution with a medical dropper to glass beads in a Buchner funnel. The saturated beads were then placed in a 60° C. oven for 15 minutes. Afterwards the beads were rinsed in a clean Buckner funnel with 100 milliliters of acetone and then returned to the oven to be dried at 60° C. until free flowing. The dry beads were then inspected under ultraviolet light in an otherwise dark room and the observed color intensity was compared to the color intensity of similarly treated glass beads whose gamma-aminopropyltriethoxy silane coating was of known thickness. The fluorescence of the unknown sample was brighter than that of the beads with a known coupling agent coating of one molecular layer, and was less bright than that of beads with a known coating of five molecular layers. From this information, it was concluded that the unknown sample had a coating thickness of between one and five layers of coupling agent.

EXAMPLE 2

In order to determine whether or not glass beads were coated with an amino functional group coupling agent, 10 grams of said beads were placed on a Buchner funnel lined with filter paper. The beads were then saturated with a solution of dansyl chloride in acetone. To accomplish the saturation, at least two milliliters of the above solution were added to the glass beads. The beads were then placed in a 60° oven for 15 minutes. Afterwards, the beads were rinsed in a clean Buchner funnel with 100 milliliters of acetone such that all yellow color was removed from the bead surface. The beads were then dried in an oven at 60° C. until they were free flowing. Next they were placed on a glass filter paper and viewed under ultraviolet light in a dark room. The observation of a yellow-green fluorescence indicated the presence of an amino functional group coating.

EXAMPLE 3

In order to determine whether or not amino functional silane coupling agent was firmly bonded to a sample of glass bead substrates, 20 grams of said beads were divided into two samples and each sample was placed on a separate buckner funnel lined with filter paper. The beads were then saturated with a solution of dansyl chloride in acetone which was added in an amount greater than two milliliters using a medicine dropper as an applicator. One sample was placed in an oven at 60° C. for 15 minutes. The second sample was left standing for 30 seconds at ambient conditions and then rinsed with 100 milliliters of acetone, such that all yellow color was removed from the bead surface. This sample was then left to dry at ambient temperatures.

After heating, the oven heated sample was rinsed in a clean buckner funnel with 100 milliliters of acetone such that all yellow color was removed from the bead surface. These beads were then oven dried at 60° C. until free flowing.

Both samples were placed on glass filter paper and viewed under untraviolet light in an otherwise dark room. The observation of a yellow-green fluorescence of similar intensity on both samples indicated the presence of a similar amount of amino functional group coating on the glass beads of both samples. Had the test sample dried under ambient conditions shown no fluorescing color or a lesser intensity of fluorescing color than the oven heated sample, this would indicate poor or incomplete covalent or chemical bonding of the coating agent to the substrate.

The terms and expressions which have been employed in each of the foregoing examples are used as terms of description and not of limitation, and there is no intention, in the use of such terms and expressions, of excluding any equivalents of the features described, or portions thereof, it being recognized that various modifications are possible within the scope of the invention claimed.

What is claimed is:

1. A method of determining the extent of chemical bonding between amino functional group coatings and inorganic substrates which comprises:
    dividing a sample of the inorganic substrate to be tested into two parts;
    saturating each part with a solution of 1-dimethylaminonaphthalene-5-sulfonyl chloride in a polar organic solvent;
    heating one part, but not the other, at a temperature and for a time sufficient to graft or condense the coating modified with the 1-dimethylaminonaphthalene-5-sulfonyl chloride onto the inorganic substrate;
    rinsing away all yellow color from both parts, the heated part after heating and the unheated part more than 30 seconds after saturating with 1-dimethylaminonaphthalene-5-sulfonyl chloride; and
    comparing, under ultraviolet light in an otherwise substantially dark room, the color intensity of the two parts of the sample.

2. A method as in claim 1 wherein the polar organic solvent is acetone.

3. A method as in claim 1 wherein a polar organic solvent is used for rinsing.

4. A method as in claim 1 wherein acetone is used for rinsing.

5. A method as in claim 1 wherein the part to be heated is heated at a temperature below 60° C.

6. A method as in claim 1 wherein the part to be heated is heated for approximately 15 minutes at between 50° C. and 60° C.

7. A method as in claim 1 wherein the substrate to be tested is comprised of glass spheres, irregular glass particles, fiberglass, mica, or alumina.

* * * * *